US008821428B2

(12) United States Patent
Tanaka et al.

(10) Patent No.: US 8,821,428 B2
(45) Date of Patent: Sep. 2, 2014

(54) TRACTION APPARATUS AND ROPE TAKE-UP MECHANISM OF TRACTION APPARATUS

(75) Inventors: Noboru Tanaka, Kounosu (JP); Yoshiharu Ootomo, Tsuchiura (JP); Toshimasa Sakagami, Tokyo (JP)

(73) Assignee: Ito Co., Ltd., Tokyo (JP)

( * ) Notice: Subject to any disclaimer, the term of this patent is extended or adjusted under 35 U.S.C. 154(b) by 1228 days.

(21) Appl. No.: 12/516,702

(22) PCT Filed: Aug. 6, 2007

(86) PCT No.: PCT/JP2007/065363
§ 371 (c)(1),
(2), (4) Date: Feb. 5, 2010

(87) PCT Pub. No.: WO2008/068928
PCT Pub. Date: Jun. 12, 2008

(65) Prior Publication Data
US 2010/0137772 A1    Jun. 3, 2010

(30) Foreign Application Priority Data

Dec. 1, 2006  (JP) .................................. 2006-325810

(51) Int. Cl.

| | |
|---|---|
| *A63B 21/005* | (2006.01) |
| *A63B 71/00* | (2006.01) |
| *A63B 22/00* | (2006.01) |
| *A61H 3/00* | (2006.01) |
| *A47D 13/04* | (2006.01) |
| *A63B 21/06* | (2006.01) |
| *A63B 26/00* | (2006.01) |
| *A61H 7/00* | (2006.01) |
| *A61F 5/00* | (2006.01) |

(52) U.S. Cl.
USPC .......... 602/33; 482/5; 482/8; 482/66; 482/93; 482/94; 482/95; 482/96; 482/131; 482/133; 482/134; 482/135; 482/136; 482/137; 482/138; 482/143; 601/23; 601/24; 602/32; 602/34; 602/35; 602/38

(58) Field of Classification Search
USPC ............ 602/32–40; 482/5, 8, 66, 93–96, 131, 482/133–138, 143; 601/23, 24
See application file for complete search history.

(56) References Cited

U.S. PATENT DOCUMENTS

| 7,563,207 B1 * | 7/2009 | Burek ............................. 482/91 |
| 7,770,744 B2 * | 8/2010 | Scharf et al. .................. 212/271 |
| 2005/0230670 A1 | 10/2005 | Kataoka |

FOREIGN PATENT DOCUMENTS

| CN | 163978 A | 0/0000 |
| JP | 56-18868 | 2/1981 |

(Continued)

OTHER PUBLICATIONS

Japanese Office Action issued on Aug. 11, 2009, for corresponding Japanese Patent Application 2006-325810.

(Continued)

*Primary Examiner* — Patricia Bianco
*Assistant Examiner* — Brandon L Jackson
(74) *Attorney, Agent, or Firm* — K&L Gates LLP

(57) ABSTRACT

A traction apparatus which impresses a desired traction force to a body to be pulled is provided. The traction apparatus includes: a traction mechanism that includes a harness coupled to the body to be pulled, a rope having one end attached to the harness, and a take-up drum attaching to an other end of the rope and impressing the traction force on the body to be pulled by taking up the rope; a first pulley that engages at a predetermined wrapping angle the rope to which the traction force is impressed by being taken up by the take-up drum, a rope load being impressed to the first pulley from the rope; a coupling plate that rotatably holds the first pulley, the rope load being impressed to the coupling plate from the first pulley; a load sensor plate that holds the coupling plate at one end portion thereof, the rope load being impressed to the load sensor from the coupling plate; an outer frame that fixes an other end portion of the load sensor plate; and a load cell adhered to a surface of the load sensor plate.

12 Claims, 4 Drawing Sheets

(56) References Cited

FOREIGN PATENT DOCUMENTS

| JP | 59-118156 | 7/1984 |
| JP | 63-032894 | 3/1988 |
| JP | 4-24588 | 2/1992 |
| JP | 3015292 | 6/1995 |
| JP | 08-280724 | 10/1996 |
| JP | 09-265348 | 10/1997 |
| JP | 2003-88540 | 3/2003 |
| JP | 2003-088540 | 3/2003 |
| JP | 2005-111113 | 4/2005 |
| JP | 2005-129414 | 5/2005 |
| WO | 2004/056689 | 7/2004 |

OTHER PUBLICATIONS

International Search Report dated Sep. 25, 2007.
Chinese Office Action issued on May 6, 2011, for corresponding Chinese Patent Application No. 2007800437789.

* cited by examiner

TRACTION APPARATUS AND ROPE TAKE-UP MECHANISM OF TRACTION APPARATUS

CROSS REFERENCE TO RELATED APPLICATIONS

The present application is a National Stage of International Application No. PCT/JP2007/065363 filed on Aug. 6, 2007 and which claims priority to Japanese Patent Application No. 2006-325810 filed on Dec. 1, 2006, the entire contents of which are being incorporated herein by reference.

BACKGROUND

The present application relates to a traction apparatus that is used as a medical treatment device to hoist the neck or waist of a human body and a rope take-up mechanism of the traction apparatus.

The traction apparatus of FIGS. 5A and 5B shows a conventional mechanism used as a medical treatment machine that hoists the neck or the waist of a human body. FIG. 5A shows a schematic configuration of the traction apparatus. FIG. 5B shows the traction apparatus shown in FIG. 5A as viewed from the direction of arrow "a".

In the conventional traction apparatus that is shown in FIG. 5A and FIG. 5B, a traction rope (also simply called a "rope") 110 that hoists a neck or a waist of a human body in the direction of arrow "c" passes along a pulley C143, a pulley B142, a pulley D144, and a pulley A141 to be led to a take-up drum 111. The rotating surface of the pulley D144 is perpendicularly disposed with respect to the rotating surface of the other pulleys A, B, and C.

In this way, the conventional traction apparatus causes the load that acts on the traction rope 110 to be transmitted to a rope take-up mechanism that is intricately combined. The load in the direction of arrow "b" applied to the pulley D144 acts on a coil spring 145 that undergoes linear displacement. The coil spring 145 contracts in proportion to the load, and the displacement is detected as a voltage change of a potentiometer 146. Thereby, the load on the rope 110 is detected. The center shaft of the take-up drum 111 is joined to a spiral spring (spring) not shown. For that reason, a constant tension always acts on the rope 110, and a level position of the rope 110 is maintained as shown in FIG. 5A and FIG. 5B without sagging.

As described above, in the conventional traction apparatus, the rope 110 is bent a number of times by a plurality of pulleys.

In order for the rope take-up drum 111 to take up the rope 110 in an orderly manner, a winding groove 111a with a semi-circular shape of the cross-section of the rope is provided in the take-up surface. The rope 110 is taken up on the take-up drum 111 along this winding groove 111a.

As a traction apparatus of this type, there has been proposed a sitting traction apparatus that is provided with a sling device for slinging up the underarms of a patient and a seat portion that has a fixture for fixing the thighs, and so by hoisting the seat portion (upper half of the patient's body) vertically, treats the lumbar and the like (for example, refer to Japanese Unexamined Patent Application, First Publication No. 2003-88540).

As a conventional traction apparatus, there has been proposed a traction apparatus that has a load cell that detects traction force, and along with detecting traction force, is constituted so as to use the detection signal for drive control of a motor that is a drive source of traction force (for example, refer to Japanese Unexamined Patent Application, First Publication No. S59-118156).

The conventional traction apparatus described above causes the rope 110 to be bent a number of times by the plurality of pulleys. Also, this traction apparatus detects the load on the rope 110 using a coil spring 145 that is attached to the pulley 144. This results in a structure in which a load is placed on the rope 110. Also, the winding groove 111a with a semi-circular shape of the cross-section of the rope is provided in the take-up surface of the take-up drum 111 for the rope 110. The rope 110 is worn by the edge of this winding groove 111a, and the life of the rope is shortened. The wearing of the rope 110 leads to the surface of the rope being cut down, whereby rope scraps are generated. As a result of these scraps entering the moving portions of a mechanism, the problem arises of causing malfunction.

SUMMARY

An object of the present invention thereof is to simplify the rope take-up mechanism that hoists a rope. Moreover, it is possible to provide a traction apparatus and a rope take-up mechanism of a traction apparatus in which there is no wearing of the rope by the edge of the winding groove on the surface of the rope take-up drum as in a conventional drum.

A traction apparatus according to an embodiment that impresses a desired traction force to a body to be pulled, includes: a traction mechanism that includes a harness coupled to the body to be pulled, a rope having one end attached to the harness, and a take-up drum attaching to an other end of the rope and impressing the traction force on the body to be pulled by taking up the rope; a first pulley that engages at a predetermined wrapping angle the rope to which the traction force is impressed by being taken up by the take-up drum, a rope load being impressed to the first pulley from the rope; a coupling plate that rotatably holds the first pulley, the rope load being impressed to the coupling plate from the first pulley; a load sensor plate that holds the coupling plate at one end portion thereof, the rope load being impressed to the load sensor from the coupling plate; an outer frame that fixes an other end portion of the load sensor plate; and a load cell adhered to a surface of the load sensor plate.

With this constitution, the first pulley, on which the rope load is impressed from the rope to which the traction force is impressed, is attached to the outer frame via the coupling plate and the load sensor plate without being directly attached to the outer frame. Also, the load cell is adhered to the load sensor plate, and the amount of strain of the load sensor plate due to the rope load is detected with this load cell.

Thereby, it is possible to detect the rope load that is impressed on the pulley with a simple constitution. It is possible to calculate the load that is being impressed on the body to be pulled from the detection value of this rope load.

For this reason, it is possible to simplify the rope take-up mechanism of the traction apparatus.

Also, the aforementioned traction apparatus may include a second pulley that engages the rope closer to the harness than the first pulley.

Thereby, it is possible to constitute the traction apparatus by using two pulleys. For this reason, it is possible to simplify the rope take-up mechanism of the traction apparatus.

Also, in the aforementioned traction apparatus, a lengthwise direction of the sensor plate may be a direction that forms equal angles with each of a first movement path of the rope from the second pulley to the first pulley and a second movement path of the rope from the first pulley to the take-up drum.

With this kind of constitution, the rope load from the first pulley is added parallel to the lengthwise direction of the load sensor plate.

For this reason, it is possible to effectively detect the rope load at the load sensor plate.

Also, in the aforementioned traction apparatus, the rope may engage the first pulley so that the first movement path and the second movement path are orthogonal.

With this kind of constitution, a rope load of $\sqrt{2}$ times the traction force is applied from the direction that forms a 45° angle with each of the first movement path of the rope from the second pulley to the first pulley and the second movement path of the rope from the first pulley to the take-up drum.

For this reason, it is possible to more effectively detect the rope load at the load sensor plate.

Also, in the aforementioned traction apparatus, the rope load may be a tensile load.

With this kind of constitution, a tensile load acts on the load sensor plate.

For this reason, it is possible to more effectively detect the rope load at the load sensor plate.

Also, the aforementioned traction apparatus may include a load sensor mechanism that includes the first pulley, the coupling plate, and the load sensor plate, the load sensor mechanism being constituted to be rotatable in compliance with a rope take-up position of the take-up drum.

With this kind of constitution, the orientation of the first pulley changes by the load sensor mechanism rotating in compliance with the rope take-up position of the take-up drum.

Thereby, it is possible to take up the rope in an orderly manner without providing a winding groove on the take-up surface of the take-up drum. For this reason, it is possible to eliminate the problem of the rope wearing on the edge of the winding groove of the surface of the take-up drum, which occurs in a conventional traction apparatus.

Also, the aforementioned traction apparatus may include a second pulley that engages the rope closer to the harness than the first pulley, the second pulley being constituted to be rotatable in compliance with movement of a first movement path of the rope from the first pulley to the second pulley accompanying rotation of the load sensor.

With this kind of constitution, the second pulley rotates in compliance with movement of the first movement path that accompanies movement of the second movement path of the rope corresponding to the take-up position of the take-up drum.

Thereby, it is possible to smooth movement from the first movement path to a third movement path at the second pulley.

Also, a rope take-up mechanism according to the embodiment of a traction apparatus impressing a desired traction force on a body to be pulled by a harness coupled to the body to be pulled and a rope having one end attached to the harness, includes: a take-up drum that attaches to an other end of the rope and that impresses the traction force on the body to be pulled by taking up the rope; a first pulley that engages at a predetermined wrapping angle the rope to which the traction force is impressed by being taken up by the take-up drum, and on which a rope load is impressed from the rope; a second pulley that engages the rope closer to the harness than the first pulley; and a load sensor mechanism that includes: a coupling plate rotatably holding the first pulley, the rope load being impressed to the coupling plate from the first pulley; a load sensor plate holding the coupling plate at one end portion thereof, the rope load being impressed to the load sensor plate from the coupling plate; an outer frame fixing an other end portion of the load sensor plate; and a load cell adhered to a surface of the load sensor plate.

With this kind of constitution, the first pulley, on which the rope load that is generated from the rope is impressed, is attached to the outer frame via the coupling plate and the load sensor plate without being directly attached to the outer frame. Also, the load cell is adhered to the load sensor plate, and the strain (strain arising from the rope load) of the load sensor plate due to the rope load is detected with this load cell.

Thereby, it is possible to detect the rope load that is impressed on the pulley with a simple constitution. It is possible to calculate the load that is being impressed on the body to be pulled from the detection value of this rope load.

For this reason, it is possible to simplify the rope take-up mechanism of the traction apparatus.

Also, in the aforementioned rope take-up mechanism of the traction apparatus, wherein a lengthwise direction of the load sensor plate may be a direction that forms equal angles with each of a first movement path of the rope from the second pulley to the first pulley and a second movement path of the rope from the first pulley to the take-up drum.

Thereby, it is possible to effectively detect the rope load at the load sensor plate.

Also, in the aforementioned rope take-up mechanism of the traction apparatus, the rope may engage the first pulley so that the first movement path and the second movement path are orthogonal.

With this kind of constitution, a rope load of $\sqrt{2}$ times the traction force in the lengthwise direction of the load sensor plate is applied from the direction that forms a 45° angle with each of the first movement path of the rope from the second pulley to the first pulley and the second movement path of the rope from the first pulley to the take-up drum.

Thereby, it is possible to more effectively detect the rope load at the load sensor plate.

Also, in the aforementioned rope take-up mechanism of the traction apparatus, the rope load may be a tensile load.

With this kind of constitution, a tensile load acts on the load sensor plate.

Thereby, it is possible to more effectively detect the rope load at the load sensor plate.

Also, in the aforementioned rope take-up mechanism of the traction apparatus, the load sensor mechanism may be constituted to be rotatable in compliance with a rope take-up position of the take-up drum, and the second pulley may be constituted to be rotatable in compliance with movement of a first movement path of the rope from the first pulley to the second pulley accompanying rotation of the load sensor.

With this kind of constitution, the orientation of the first pulley changes by the load sensor mechanism rotating in compliance with the rope take-up position of the take-up drum. Also, the second pulley rotates in compliance with rotation of the first pulley corresponding to the take-up position of the take-up drum.

Thereby, it is possible to take up the rope in an orderly manner without providing a winding groove on the rope take-up surface of the take-up drum. For this reason, it is possible to eliminate the problem of the rope wearing on the edge of the winding groove of the surface of the take-up drum, which occurs in a conventional traction apparatus.

Also, since the second pulley is capable of rotating, it is possible to smooth movement at the second pulley from the first movement path of the rope to a third movement path of the rope that changes in accordance with the take-up position of the take-up drum.

Accordingly, the traction apparatus according to the embodiment can simplify the rope take-up mechanism that hoists a rope.

Additional features and advantages of the present application are described in, and will be apparent from, the following Detailed Description and the figures.

DETAILED DESCRIPTION

Figure 1:
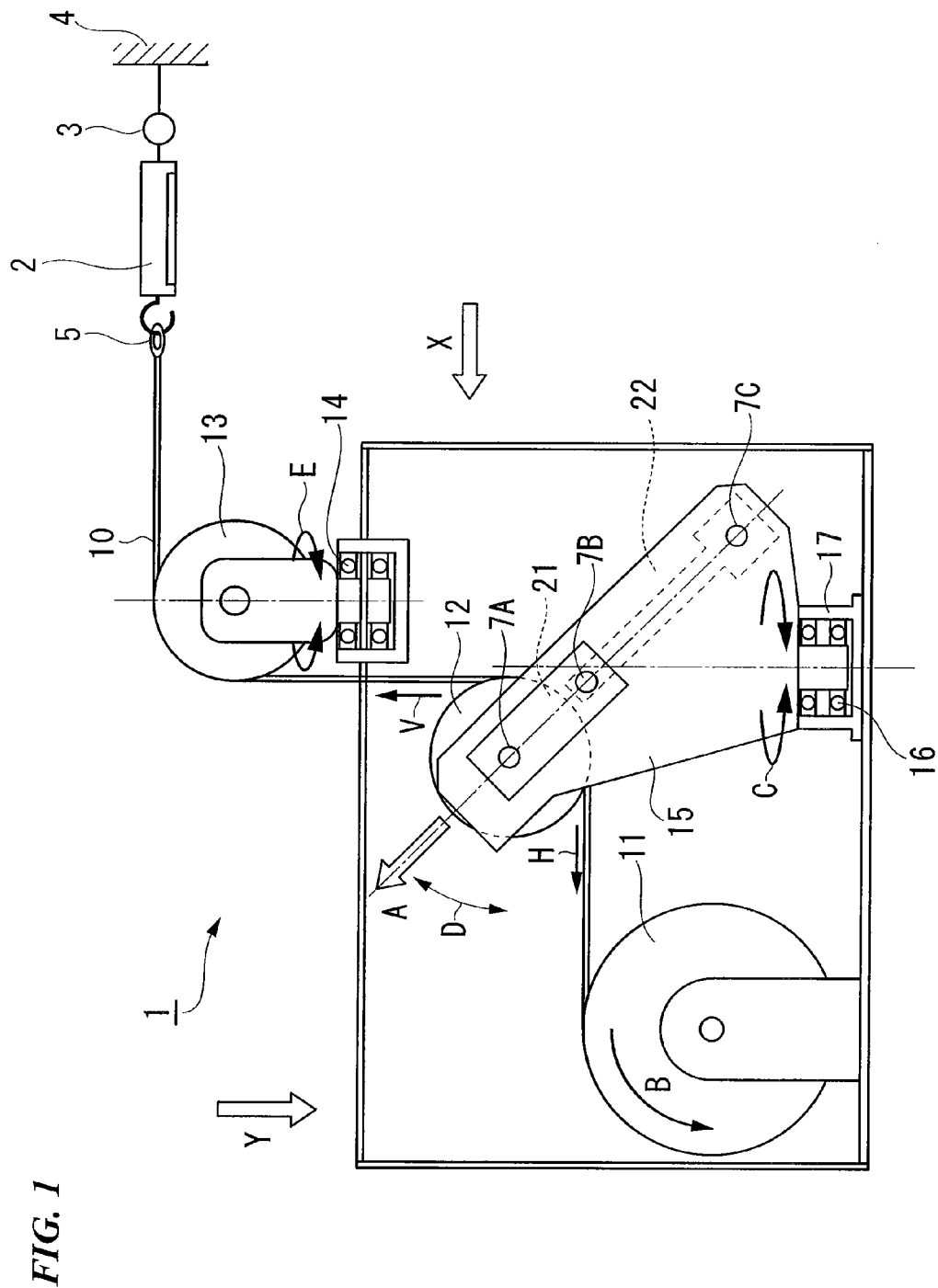
FIG. 1 is a view that shows a constitutional example of a traction apparatus according to an embodiment.

FIG. 1 shows an example of the traction apparatus according to an embodiment.

Figure 2:
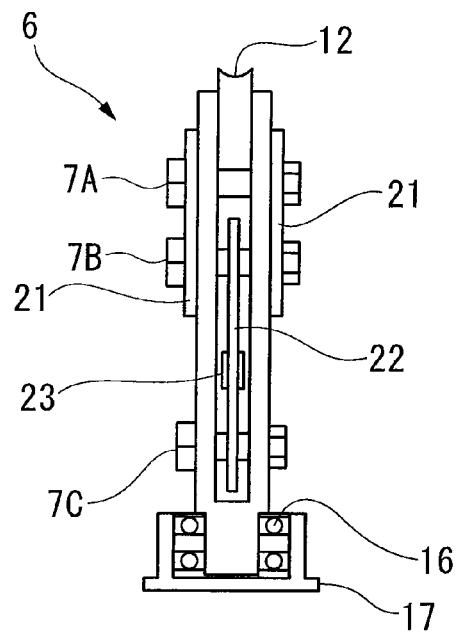
FIG. 2 is a view of a load sensor mechanism of the traction apparatus shown in FIG. 1 as viewed from direction X of FIG. 1.

A traction apparatus 1 shown in FIG. 1 is used as a medical treatment device that hoists the neck or waist of a human body. FIG. 1 is a view that shows a schematic constitution of the traction apparatus 1, and FIG. 2 is a view of a load sensor mechanism of the traction apparatus 1 shown in FIG. 1 as viewed from direction of arrow X.

In the traction apparatus 1 shown in FIG. 1, a rope 10 is coupled via a harness 5 to a body to be pulled 2 that is connected to a fixture 3 of a fixing portion 4. The body to be pulled 2 is schematically shown in FIG. 1, but is a neck or waist of a patient, or the like.

In this traction apparatus 1, the body to be pulled 2 (the traction body such as the neck or waist of the patient) is attached via the harness 5 to one end of the traction rope 10 (also simply called a "rope"). The rope 10 is coupled to a rope take-up drum 11 that holds the other end of the traction rope 10 via a second pulley 13 and a first pulley 12. The rope 10 is pulled by a traction force that is produced by rotating the take-up drum 11 in the direction of arrow B of FIG. 1 with a motor (not shown).

The movement path of the rope from one end of the rope 10 that is attached to the harness 5 that is coupled to the body to be pulled 2 to the other end of the rope 10 that is attached to the take-up drum 11 is called the total movement path. This total movement path consists of a first movement path, a second movement path, and a third movement path. The first movement path denotes the movement path of the rope from the second pulley 13 to the first pulley 12. The second movement path denotes the movement path of the rope from the first pulley 12 to the take-up drum 11. The third movement path denotes the movement path of the rope from the one end at which the harness 5 is attached to the second pulley 13.

The first pulley 12 is fixed to a pair of coupling plates 21 with a bolt 7A. The coupling plates 21 are attached to a load sensor plate 22 by a bolt 7B. The load sensor plate 22 is anchored to an outer frame 15 by a bolt 7C. That is, the pulley 12 is attached to the outer frame 15 via the coupling plates 21 and the load sensor plate 22, and not directly attached to the outer frame 15

In the above constitution, a load that is impressed on the rope 10 is applied to the pulley 12 that is attached to the outer frame 15. A load in a leftward horizontal direction (the direction of arrow H) and a load in an upward vertical direction (the direction of arrow V) are applied to the pulley 12. Accordingly, since the pulley 12 is coupled with the load sensor plate 22 via the coupling plates 21, the load that acts on the pulley 12 is applied to the load sensor plate 22 to which a load cell 23 is adhered. The lengthwise direction of the load cell plate 22 is arranged in a direction that forms a 45° angle (angle of arrow D) with the horizontal direction H (the second movement path) and the vertical direction V (first movement path). The magnitudes of the force in this horizontal direction and the force in the vertical direction are equal. Accordingly, the resultant force of the horizontal direction force and the vertical direction force is the load in the direction of A in FIG. 1. The rope load that acts on the load sensor plate 22, which is resultant force, is $\sqrt{2}$ times the load that is impressed on the rope 10. Here, the rope load refers to the load that is applied to the first pulley 12 from the rope 10. The rope load is proportional to the traction force that is impressed on the body to be pulled. This proportionality factor is computable from the relation between the direction of the first movement path and the direction of the second movement path added from the rope 10 via the first pulley 12 as mentioned above, and the lengthwise direction of the load sensor plate 22.

The lower end part of the load sensor plate 22 is coupled by the bolt 7C to the outer frame 15. The outer frame 15 is rotatably installed on a case foundation 17 through a rotary bearing 16. When strain due to the rope load is produced on the load cell 23 that is adhered to the load sensor plate 22, the amount of this strain is converted to a voltage signal through a power supply and an amplifier that are connected to the load cell 23.

In this traction apparatus 1, the outer frame 15 is constituted to be rotatable in the direction of arrow C by the rotation mechanism due to the rotary bearing 16. Accordingly, the outer frame 15 can rotate in agreement with the take-up position of the rope 10 on the take-up surface of the take-up drum 11. As a result of the second movement path of the rope 10 moving in compliance with the take-up position of the take-up drum 11, the outer frame 15 can rotate. As a result of the outer frame 15 rotating in this way, the rope 10 can be wound in an orderly manner from an end of the rope take-up drum 11 that has a cylindrical take-up surface with no winding groove. As described above, in the present embodiment, it is possible to use a take-up drum that has a linear take-up cross-section with no winding groove. For this reason, there is no wear on the rope 10 by the edge of a winding groove for rope take-up as in a conventional drum.

In accordance with the rotation of the outer frame 15, the first pulley 12, which is a constituent element of the load sensor mechanism 6, rotates. Due to this rotation, the first movement path of the rope 10 also moves. Due to the movement of this first movement path, the third movement path of the rope 10 also moves. Here, the second pulley 13 causes the rope 10 to move from the third movement path to the first movement path. This pulley 13 is rotatable in the direction of the arrow E by a rotary bearing 14. Accordingly, the pulley 13 can rotate in accordance with the movement of the aforementioned first movement path and the third movement path. Due to this rotation, it is possible to make the rope 10 smoothly move from the third movement path to the first movement path at the pulley 13.

The center axis of the take-up drum 11 is joined to a spiral spring (spring) not shown. Due to this spiral spring, since a constant tension always acts on the rope 10, a level position of the rope 10 is maintained as shown in FIG. 1 with no sagging.

The path to the load that is generated in the traction rope 10 being impressed on the load cell 23 shall be described with reference to FIG. 2.

In FIG. 2, first a load in a 45° direction (direction A in FIG. 1) that is added from the traction rope 10 is impressed on the pulley 12. The rope load that is impressed from this rope is impressed on the coupling plates 21 via the bolt 7A. The coupling plates 21 are coupled to the load sensor plate 22 via the bolt 7B. For this reason, the load that is generated in the traction rope 10 is impressed on the load sensor plate 22. Since the load cell 23 is adhered to the surface of the load sensor plate 22, strain corresponding to the rope load is generated in the load cell 23. This strain is converted to resistance change of the load cell 23. The change in resistance (change of load) of the load cell 23 is detected as a voltage change by the power supply and the amplifier that are connected to the load cell 23.

Holes are formed at the portions where the bolt 7A and the bolt 7B pass in the side surfaces of the outer frame 15 of the load sensor mechanism 6, being formed larger than the contour of the bolts 7A and 7B. Accordingly, the bolts 7A and 7B do not make contact with the outer frame 15. For this reason, a load that is added to the pulley 12 is not distributed to the outer frame 15 by the bolts 7A and 7B.

The bolt 7C is coupled to the outer frame 15. Accordingly, due to the rope load that is added to the load sensor plate 22, the bolt 7B and the bolt 7C pull the load sensor plate 22 in mutually opposite directions. As a result, strain due to the tensile stress is produced in the load sensor plate 22.

Figure 3:
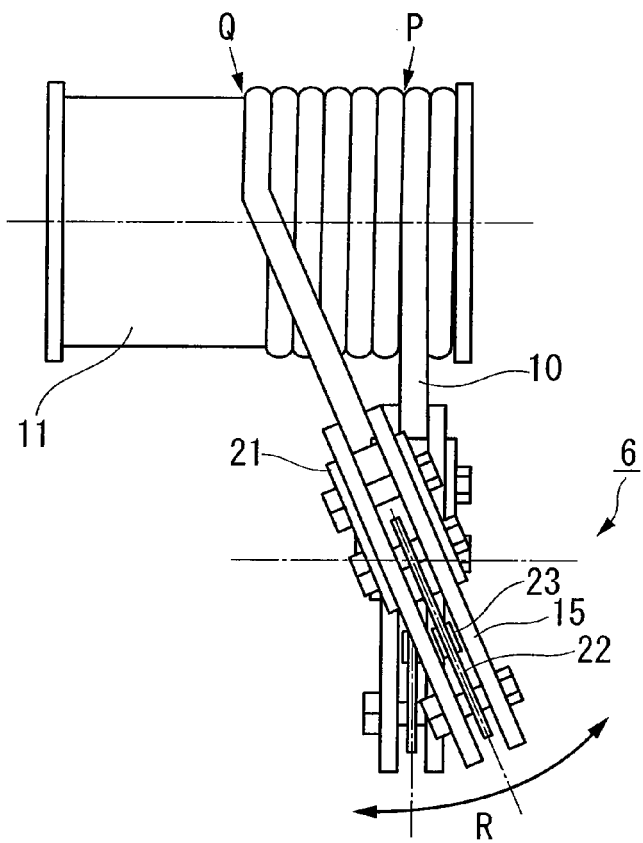
FIG. 3 is a view that shows a rope take-up mechanism according to the embodiment shown in FIG. 1.

FIG. 3 is a view that shows the rope take-up mechanism according to the embodiment. FIG. 3 is a view of the traction apparatus 1 shown in FIG. 1 as viewed from the direction of arrow Y.

In FIG. 3, the load sensor mechanism 6 includes the first pulley 12 and a mechanism that detects the load added to the pulley 12 with the load cell 23. The load sensor mechanism 6 rotates by the rotary bearing 16. The load sensor mechanism 6 rotates in the direction of arrow R in accordance with the position at which the rope 10 on the take-up surface of the take-up drum 11 is wound on the drum (for example, the position of arrow P, the position of arrow Q) as shown in FIG. 3. By doing so, the rope 10 can be wound on the take-up drum 11 in an orderly manner without miming up on the neighboring rope. The start of winding of the rope 10 on the take-up drum 11 is the right end of the take-up drum surface. At this right end, a hole that passes the rope is provided heading to the center of the take-up drum. The interior of the take-up drum 11 is a pipe-shaped hollow. In this hollow a knot is made at one end of the rope that is inserted from the hole that passes the rope. This knot prevents the rope 10 from being pulled out when being pulled by the motor driving.

Figure 4:
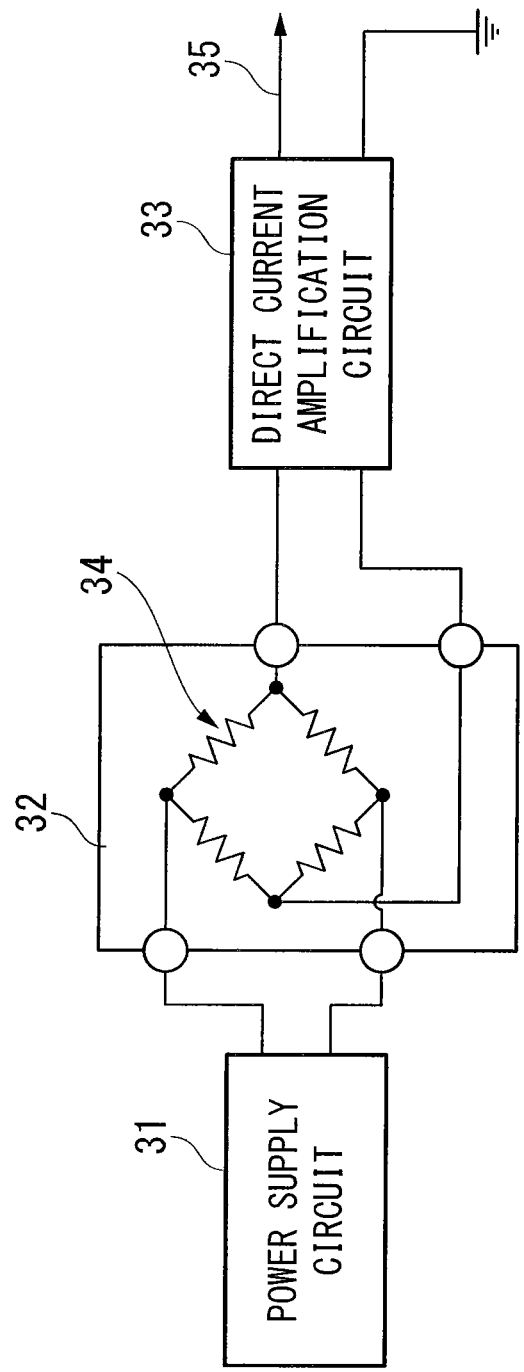
FIG. 4 is a view that shows a load detection circuit by a load cell according to the embodiment shown in FIG. 1.
Figure 5A:
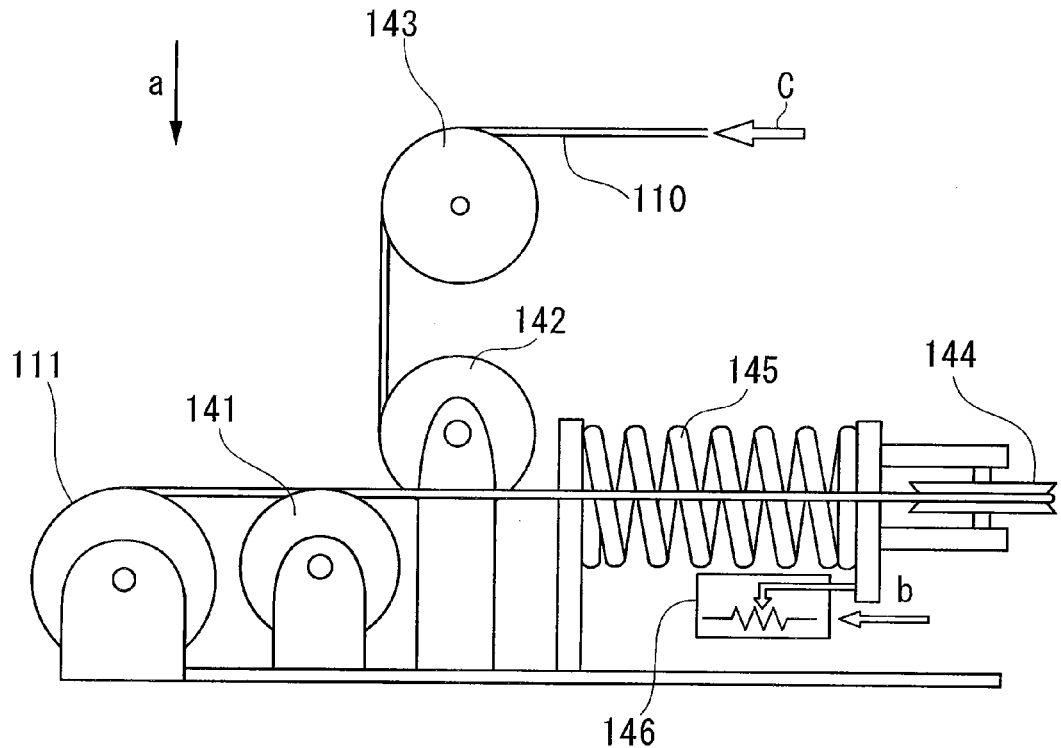
FIG. 5A is a view that shows an example of a conventional traction apparatus.
Figure 5B:
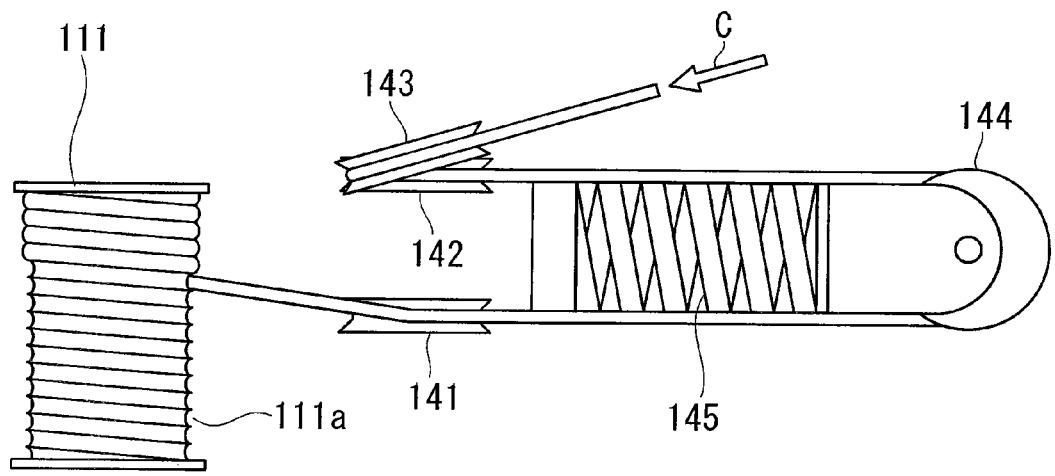
FIG. 5B is a view of the conventional traction apparatus shown in FIG. 5A as viewed from direction a in FIG. 5A.

FIG. 4 shows a constitutional example of the load detection circuit by the load cell according to the embodiment. As described above, the rope load that is proportional to the load that acts on the traction rope 10 is added as a force in the pulling direction. The load cell 23 that is adhered to this load sensor plate 22 constitutes a bridge circuit 34 as shown in FIG. 4. The strain that is produced by the load sensor plate 22 being pulled is transmitted to the load cell 23. A power supply circuit 31 is provided that supplies a stable fixed voltage to the bridge circuit 34 in order to operate this bridge circuit 34. Normally a voltage of about 10 V is supplied to the bridge circuit 34 from this power supply circuit 31. For example, in the case of the input resistance of the bridge circuit 34 being 350Ω, a power supply is used that has a current capacity sufficiently capable of providing a current that flows to this circuit.

When strain is produced in the load cell 23, an output voltage 35 of the bridge circuit 34 changes. This change in voltage is input to a direct current amplifier 33. This input is output after an offset voltage and amplification degree are arbitrarily set, and converted to a voltage signal corresponding to the load output. The motor that rotatively drives the take-up drum 11 is controlled by this voltage signal. In this way, it is possible to obtain the target traction force.

The present invention can be applied to a traction apparatus that is used as medical treatment device that hoists the neck or the waist of a human body. According to this traction apparatus, it is possible to simplify a rope take-up mechanism that hoists a rope.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A traction apparatus that impresses a desired traction force to a body to be pulled, the traction apparatus comprising:
    a traction mechanism that includes a harness coupled to the body to be pulled, a rope having a first end attached to the harness, and a take-up drum attached to a second end of the rope and impressing the traction force on the body to be pulled by taking up the rope;
    a first pulley that engages, at a predetermined wrapping angle, the rope to which the traction force is impressed by being taken up by the take-up drum, a rope load being impressed to the first pulley from the rope;
    a coupling plate that rotatably holds the first pulley, the rope load being impressed to the coupling plate from the rope via the first pulley;
    a load sensor plate that holds the coupling plate at a first end portion thereof, the rope load being impressed to the load sensor plate from the rope via the first pulley and the coupling plate;
    an outer frame that fixes a second end portion of the load sensor plate;
    a load cell adhered to a surface of the load sensor plate, the load cell detecting an amount of strain of the load sensor plate caused by the rope load; and
    a rotation mechanism that rotates the outer frame in agreement with a take-up position of the rope on a take-up surface of the take-up drum,
    the first pulley rotating in accordance with rotation of the outer frame.

2. The traction apparatus according to claim 1, comprising a second pulley that engages the rope closer to the harness than the first pulley.

3. The traction apparatus according to claim 2, wherein a lengthwise direction of the load sensor plate is a direction that forms equal angles with each of a first movement path of the rope from the second pulley to the first pulley and a second movement path of the rope from the first pulley to the take-up drum.

4. The traction apparatus according to claim 3, wherein the rope engages the first pulley so that the first movement path and the second movement path are orthogonal.

5. The traction apparatus according to claim 1, comprising a load sensor mechanism that includes the first pulley, the coupling plate, and the load sensor plate, wherein the load sensor mechanism is configured to be rotatable in compliance with a rope take-up position of the take-up drum.

6. The traction apparatus according to claim 5, comprising a second pulley that engages the rope closer to the harness than the first pulley, the second pulley is configured to be rotatable in compliance with movement of a first movement path of the rope from the first pulley to the second pulley accompanying rotation of the load sensor.

7. The traction apparatus according to claim 1, wherein the rope load is a tensile load.

8. A rope take-up mechanism of a traction apparatus impressing a desired traction force on a body to be pulled by a harness coupled to the body to be pulled and a rope having a first end of the rope attached to the harness, the rope take-up mechanism comprising:
- a take-up drum that attaches to a second end of the rope and that impresses the traction force on the body to be pulled by taking up the rope;
- a first pulley that engages, at a predetermined wrapping angle, the rope to which the traction force is impressed by being taken up by the take-up drum, and on which a rope load is impressed from the rope;
- a second pulley that engages the rope closer to the harness than the first pulley;
- a load sensor mechanism that includes: a coupling plate rotatably holding the first pulley, the rope load being impressed to the coupling plate from the rope via the first pulley; a load sensor plate holding the coupling plate at a first end portion thereof, the rope load being impressed to the load sensor plate from the rope via the first pulley and the coupling plate; an outer frame fixing a second end portion of the load sensor plate; and a load cell adhered to a surface of the load sensor plate, the load cell detecting an amount of strain of the load sensor plate caused by the rope load; and
- a rotation mechanism that rotates the outer frame in agreement with a take-up position of the rope on a take-up surface of the take-up drum,
- the first pulley rotating in accordance with rotation of the outer frame.

9. The rope take-up mechanism of the traction apparatus according to claim 8, wherein a lengthwise direction of the load sensor plate is a direction that forms equal angles with each of a first movement path of the rope from the second pulley to the first pulley and a second movement path of the rope from the first pulley to the take-up drum.

10. The rope take-up mechanism of the traction apparatus according to claim 9, wherein the rope engages the first pulley so that the first movement path and the second movement path are orthogonal.

11. The rope take-up mechanism of the traction apparatus according to claim 8, wherein the rope load is a tensile load.

12. The rope take-up mechanism of the traction apparatus according to claim 8, wherein the load sensor mechanism is configured to be rotatable in compliance with a rope take-up position of the take-up drum, and
- the second pulley is configured to be rotatable in compliance with movement of a first movement path of the rope from the first pulley to the second pulley accompanying rotation of the load sensor.

* * * * *